United States Patent
Proksa et al.

(10) Patent No.: US 10,575,391 B2
(45) Date of Patent: Feb. 25, 2020

(54) DETERMINING A STATUS OF AN X-RAY TUBE OF AN X-RAY SYSTEM

(71) Applicant: KONINKLIJKE PHILIPS N.V., Eindhoven (NL)

(72) Inventors: Roland Proksa, Neu Wulmstorf (DE); Rolf Karl Otto Behling, Norderstedt (DE); Carolina Ribbing, Aachen (DE); Lester Donald Miller, Hudson, OH (US); Alexander Eitel, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 43 days.

(21) Appl. No.: 15/779,105

(22) PCT Filed: Nov. 18, 2016

(86) PCT No.: PCT/EP2016/078106
§ 371 (c)(1),
(2) Date: May 25, 2018

(87) PCT Pub. No.: WO2017/093045
PCT Pub. Date: Jun. 8, 2017

(65) Prior Publication Data
US 2018/0270939 A1 Sep. 20, 2018

Related U.S. Application Data

(60) Provisional application No. 62/261,385, filed on Dec. 1, 2015.

(30) Foreign Application Priority Data

Feb. 4, 2016 (EP) ...................................... 16154244

(51) Int. Cl.
*H05G 1/54* (2006.01)
*A61B 6/00* (2006.01)

(52) U.S. Cl.
CPC ................ *H05G 1/54* (2013.01); *A61B 6/586* (2013.01)

(58) Field of Classification Search
CPC ........... A61B 6/40; A61B 6/405; A61B 6/586; H05G 1/54
See application file for complete search history.

(56) References Cited

U.S. PATENT DOCUMENTS 5,103,470 A * 4/1992 Iwamoto .............. G01N 23/223
250/370.01
7,302,041 B2  11/2007 Deuringer
(Continued)

FOREIGN PATENT DOCUMENTS

WO  WO2015032664 A1  3/2015

OTHER PUBLICATIONS

Fukuda Atsushi et al: "Long-Term Stability of Beam Quality and Output of Conventional X-Ray Units", Radiological Physics and Technology, Springer Japan KK, JP, vol. 8, No. 1, Jul. 29, 2014 (Jul. 29, 2014), pp. 26-29, XP035426934.

*Primary Examiner* — Marcus H Taningco
(74) *Attorney, Agent, or Firm* — Larry Liberchuk

(57) ABSTRACT

The present invention relates to a device (34) and a method (70) for determining a status of an X-ray tube (10) of an X-ray system (36). Due to ageing and/or wear of the X-ray tube, the spectrum of the X-ray radiation (30) provided by the X-ray tube may change over the operation time of the X-ray tube. The present invention therefore suggests evaluating spectrally different values detected with an X-ray detector arrangement (32) of the X-ray system. A reference data set representing a reference condition of the X-ray tube by a plurality of spectrally different reference-values (44) and a working data set representing an aged condition of the X-ray tube by a plurality of spectrally different working-values (46) of detected X-ray radiation are used to determine (Continued)

an equivalent filtration function for an filtration material influencing a source X-ray radiation (26) emitted by an anode (16) of the X-ray tube. Accordingly, the filtration function provides the information about the material being used for the filtration and/or its length, which may provide the basis to determine the condition and thus the status of the X-ray tube.

11 Claims, 6 Drawing Sheets

(56) References Cited

U.S. PATENT DOCUMENTS

2013/0083901 A1    4/2013  Grasruck
2014/0177810 A1*   6/2014  Gao .......................... H05G 1/54
                                                              378/207

* cited by examiner

DETERMINING A STATUS OF AN X-RAY TUBE OF AN X-RAY SYSTEM

FIELD OF THE INVENTION

The present invention relates to a device and a method for determining a status of an X-ray tube of an X-ray system, an X-ray imaging system comprising the device, a computer program element and a computer-readable medium.

BACKGROUND OF THE INVENTION

An X-ray system comprises an X-ray tube for providing an X-ray radiation. The X-ray radiation can pass through an object to be imaged. The X-ray radiation passing the object can thereafter impinge upon an X-ray detector in order to generate an image of the object. X-ray systems may be used in operating room environments or for radiology diagnostics. However, X-ray systems may be used for other purposes, too.

An X-ray tube may be subject to wear during use, which may result in an impact to the X-ray radiation provided by the X-ray tube. With an increasing wear of the X-ray tube a failure probability of the X-ray tube may increase also. Failure of an X-ray tube, in particular if a failure occurs while using the X-ray tube for performing X-ray imaging with the corresponding X-ray system, is highly undesirable. Therefore, it would be desirable to provide a status of the X-ray tube, which may indicate the condition of the X-ray tube.

Document DE 103 38 693 B3 relates to a method for estimate the lifetime of an X-ray source. The X-ray radiation provided by the X-ray source is compared with an X-ray threshold value and the result thereof is used to determine the remaining lifetime of the X-ray source.

Document US 2013/0083901 A1 discloses a method and a device for determining the wear of an X-ray anode.

Document US 2014/0177810 A1 discloses a system and method for estimating and compensating for anode target filtration in an X-ray tube.

Document WO 2015/032664 A1 discloses an X-ray tube housing assembly which allows the correction of degradation over time because of the action of the electron beam altering the surface of the focal spot area of a rotating anode.

SUMMARY OF THE INVENTION

There may be a need to provide an enhanced prediction about the condition of an X-ray tube of an X-ray system.

The object of the present invention is solved by the subject-matter of the independent claims, wherein further embodiments are incorporated in the dependent claims. It should be noted that the following described aspects of the invention apply also for the device, the system, the method, the computer program element and the computer-readable medium.

According to a first aspect of the invention, a device for determining a status of an X-ray tube of an X-ray system is provided, comprising an input interface, an output interface and a processing unit. The input interface is configured to receive a reference data set representing a plurality of spectrally different reference-values of a detected X-ray radiation of an X-ray tube under a predefined control scheme of an X-ray system. The input interface is configured to receive a working data set representing a plurality of spectrally different working-values of a detected X-ray radiation of the X-ray tube under the same predefined control scheme of the X-ray system, wherein an X-ray filtration, caused by a use of the X-ray tube, is applied at the X-ray radiation path of the X-ray tube. The processing unit is configured to determine, based on the reference data set and the working data set, a filtration function for the X-ray radiation of the X-ray tube indicating the X-ray filtration. The processing unit is configured to determine a status of the X-ray tube based on the filtration function. The output interface is configured to provide the status of the X-ray tube for a further purpose. The processing unit is configured to determine, based on the filtration function, an absorption spectrum; and wherein the processing unit is configured to determine the status of the X-ray tube based on the absorption spectrum.

In an example, spectrally different values may indicate or represent energies at different energy sub-spectrums of the X-ray radiation. For instance, one value of a set may represent the detected X-ray radiation at a first X-ray tube voltage, for example of 80 kVp, wherein a further value of the same set may represent the detected X-ray radiation at a second X-ray tube voltage, for example of 140 kVp.

In an example, the control scheme may relate to settings for the X-ray system, in particular for the X-ray tube, and/or to an operation plan for the X-ray system.

In an example, the reference-values and the working-values are acquired at different times, wherein the X-ray system is controlled each time in accordance with the control scheme.

Thus, the same settings for the X-ray system and/or the same operation plan may be applied to the X-ray system.

In a further example, the reference-values may indicate values of detected X-ray radiation, when the X-ray tube is new or has a reference condition.

In a further example, the working-values may be detected after the use of the X-ray system, in particular after certain operation times of the X-ray tube and/or of the X-ray system.

In an example, the X-ray filtration may be caused by an X-ray filtration material accumulated during the use of the X-ray tube and arranged at the X-ray radiation path of the X-ray tube. The X-ray radiation path of the X-ray tube may the path between an anode of the X-ray tube and an outer surface of an output window of the X-ray tube.

In an example, the X-ray filtration may relate to a heel effect at the anode, a material filtration at the output window and/or any filtration due to wearing. The filtration may be due to ageing of the cathode, the anode, the bearing of the anode and/or any other wear of the X-ray tube.

In an example, the reference data set may be provided to the input interface of the device, in particular by a storage means, which may be part of the device.

As an effect, the working data set may refer to a spectrum of the detected X-ray radiation, which may have undergo a filtration, in particular with a filtration material due to ageing or wearing of the X-ray tube.

As a further effect, a difference between the reference spectrum, indicated by the reference data set, and a working spectrum, indicated by the working data set, may be equivalent to the filtration. Accordingly, a filtration function, preferably as an estimation for the actual filtration function, can be determined based on the reference data set and the working data set.

As a further effect, the filtration function may depend on the kind or type of the X-ray filtration. For example, an anode material filtration, in particular a tungsten material filtration, can cause a different filtration function as a cathode material filtration. In a further example, the status of the X-ray tube may be determined based on the type of the X-ray filtration and/or an extent of the X-ray filtration.

As an effect, the filtration function provides a good basis to determine the status of the X-ray tube, since the filtration function allows to more precisely determine the wear and/or any other ageing of the X-ray tube.

As described above, in the present invention, the processing unit is configured to determine, based on the filtration function, an absorption spectrum, wherein the processing unit is configured to determine the status of the X-ray tube based on the absorption spectrum.

In an example, the spectrum refers to an energy spectrum.

In an example, the filtration causes the absorption spectrum, which may serve as the basis, or as a part thereof, to determine the status of the X-ray tube.

In an example, energy resolving measurements may be modeled with a set of equations, wherein each equation $$d_i \cong I_i \int_0^\infty R_i(E) D_i(E) F_i(E) e^{-Ls(E)} dE$$

is an estimation of one detector response, wherein
di relates to the expected detector signal of measurement i,
Ii relates to the x-ray tube current of measurement i,
Ri(E) relates to the emission spectrum for measurement i (without the unknown filter effect),
Di(E) relates to the spectral detector response for measurement i,
Fi(E) relates to optional filtration spectra for measurement i,
L relates to the length of the unknown filter material, and
s(E) relates to the absorption spectrum of the unknown.

In an example, with this model and a set of detector measurements $d_i \leftarrow \tilde{d}_i$, the absorption spectrum and/or the absorption length may be determined.

As an effect, the absorption spectrum may indicate a certain filtration, in particular the type of the filtration and/or the extent of the filtration, which allows an enhanced estimation about the condition and thus about the status of the X-ray tube.

According to a further exemplary embodiment of the present invention, the processing unit is configured to determine, based on the filtration function, an absorption length, wherein the processing unit is configured to determine the status of the X-ray tube based on the absorption length.

As an effect, the absorption length, which may influence the filtration, provides a good basis for the determination of the status of the X-ray tube.

In an example, the filtration may also correspond to the absorption length of a filtration material, which may be arranged at the X-ray radiation path of the X-ray tube. Therefore, the absorption length may serve as the basis, or as a part thereof, to determine the status of the X-ray tube.

According to a further exemplary embodiment of the present invention, the processing unit is configured to determine a further data set corresponding to a ratio of the reference data set and the working data set, or vice versa, wherein the processing unit is configured to determine the filtration function based on the further data set.

As an effect, the further data set may be X-ray flux independent and thus may provide a good basis for determining the filtration function.

According to a further exemplary embodiment of the present invention, the processing unit is configured to determine, based on the filtration function, an absorption material, wherein the processing unit is configured to determine the status of the X-ray tube based on the absorption material.

As an effect, the filtration can also correspond to an absorption material causing the filtration, which may also serve as a good basis, or as a part thereof, to determine the status of the X-ray tube.

In an example, determining oil or lead as the absorption material may indicate a failure of the X-ray tube, in particular which may cause to interrupt the use of the X-ray tube. Thus, determining a certain absorption material as such may provide a basis to determine the status of the X-ray tube.

According to a second aspect of the present invention, an X-ray system is provided, comprising an X-ray tube, an X-ray detector arrangement, an X-ray system controller and a device as described above. The X-ray system controller is configured to control the X-ray system according to the control scheme.

In an example, the X-ray system is configured as an X-ray imaging system. In an example, the X-ray system controller is configured to control the X-ray system with predefined settings for the X-ray system, in particular for the X-ray tube, in accordance with the control scheme and/or to control the X-ray system with an operation plan in accordance with the control scheme.

As an effect, the reference data set and the working data set may be acquired under equivalent conditions.

According to an exemplary embodiment of the system according to the present invention, the X-ray detector arrangement is configured to detect the X-ray radiation of the X-ray tube under the control scheme resulting in the plurality of spectrally different working-values.

As an effect, the X-ray detector arrangement can provide the working-values and/or the working data set to the input interface of the device.

According to a further exemplary embodiment of the system according to the present invention, the X-ray system controller is configured to control the X-ray systems in accordance with the control scheme, such that different X-ray tube voltages, which correspond to different X-ray tube voltages applied for detecting the reference-values, are subsequently applied for detecting the working-values.

As an effect, a plurality of spectrally different working-values can be detected, wherein at each X-ray tube voltage at least one corresponding working-value can be detected.

As an effect, the working-values may represent different values of an energy spectrum.

According to a further exemplary embodiment of the system according to the present invention, the X-ray detector arrangement comprises a plurality of X-ray detector layers, wherein the X-ray system controller is configured to control the X-ray system in accordance with the control scheme, wherein the X-ray detector layers comprise different effective responses, such that each X-ray detector layer provides a detector sub-signal representing one of the working-values.

In an example, the effective responses relate to corresponding energy sensitivities with respect to the X-ray radiation to be detected.

As an effect, an energy resolved measurement can be provided.

In an example, the X-ray detector layers differ in their ability to detect X-ray radiation, in particular with regard to the energy of the X-ray radiation.

As an effect, the X-ray detector arrangement is configured to provide a reliable basis to detect the X-ray radiation of the X-ray tube under equivalent conditions with respect to the reference data set and the working data set.

According to an exemplary embodiment of the system according to the present invention, the X-ray detector arrangement comprises a photon counting detector with energy discrimination configured to detect individual X-ray photons, to estimate its photo energy and to count these photons in respective energy bins, each representing an energy interval.

In an example, the energy bins fit to the estimated photo energies. As an effect, detecting the X-ray radiation with resolved energy is simplified.

According to a third aspect of the present invention, a method for determining a status of an X-ray tube of an X-ray system is provided, comprising the steps of:
a) providing a reference data set representing a plurality of spectrally different reference-values of a detected X-ray radiation of an X-ray tube under a predefined control scheme of an X-ray system;
b) providing a working data set representing a plurality of spectrally different working-values of a detected X-ray radiation of the X-ray tube under the same predefined control scheme of the X-ray system, wherein an X-ray filtration, caused by a use of the X-ray tube, is applied at an X-ray radiation path of the X-ray tube;
c) determining, based on the reference data set and the working data set, a filtration function for the X-ray radiation of the X-ray tube indicating the X-ray filtration;
d) determining a status of the X-ray tube based on the filtration function; and
e) providing the status of the X-ray tube for a further purpose.

According to a fourth aspect of the present invention, a computer program element for controlling a device or system as described above which, when being executed by a processing unit, is adapted to perform the method steps as described above.

According to a fifth aspect of the present invention, a computer-readable medium having stored the computer program element is provided.

According to an aspect of the present invention, a device and a method for determining a status of an X-ray tube of an X-ray system is provided. The X-ray tube usually comprises a cathode and an anode. The anode and the cathode are arranged in a tight chamber of the X-ray tube. X-ray radiation emitted by the anode may pass through an output window at a sidewall of the chamber resulting in an X-ray radiation provided by the X-ray tube. The X-ray system further comprises an X-ray detector arrangement. At least a part of the X-ray radiation provided by the X-ray tube is directed to the X-ray detector arrangement. Thus, an object to be imaged can be placed between the X-ray tube and the X-ray detector arrangement for imaging a purpose.

Due to ageing and/or wear of the X-ray tube, the spectrum of the X-ray radiation provided by the X-ray tube may change over the operation time of the X-ray tube. The change in the spectrum of the X-ray radiation provided by the X-ray tube may be caused by tungsten disposed on the output window of the X-ray tube. The anode may be made at least partly from tungsten. Under heavy electron bombardment of the cathode, some tungsten may be able to escape from the anode. Some of this escaped tungsten atoms may be disposed on the output window of the X-ray tube. Further, the anode surface may become rough or rougher due to the escape of tungsten atoms. This is known as the so-called heel effect. Both aspects as described before may change the spectrum of the X-ray radiation provided by the X-ray tube, because the tungsten disposed on the output window as well as a rough surface of the anode may cause a source X-ray radiation emitted by the anode to transverse tungsten, in particular directly at the surface of the anode and/or the tungsten at the output window, which is equivalent to a tungsten filtration. Thus, with an increased age of the X-ray tube, the tungsten filtration may increase also and thus causes to change the spectrum of the X-ray radiation provided by the X-ray tube.

Further, the anode may be configured as a rotating anode, wherein the anode is mounted with a bearing at a casing of the X-ray tube. In particular, the bearing is spiral-groove bearing, which may use a liquid metal, in particular gallium-indium-tin. A leakage of the liquid metal in the bearing may cause a deposit of the liquid metal at the output window. Again, the output spectrum of the X-ray radiation provided by the X-ray tube may be effected by the liquid metal equivalent to a liquid metal filtration.

Further, wear of the X-ray tube, in particular from the catheter, may cause similar effects and a respective filtration and therefore a change of the output spectrum of the X-ray radiation provided by the X-ray tube.

The present invention therefore relates to an evaluation of spectrally different values detected with an X-ray detector arrangement of the X-ray system. In detail, a reference data set representing a plurality of spectrally different reference-values and a working data set representing a plurality of spectrally different working-values of detected X-ray radiation are used to determine the filtration applied to the source X-ray radiation emitted by the anode of the X-ray tube. In this respect, a filtration function can be determined which may represent the filtration, in particular the material for the filtration and/or its length in the direction of an X-ray radiation path between the anode of the X-ray tube and the X-ray detector arrangement. Accordingly, the filtration function provides the information about the material being used for the filtration and/or its length, which may provide the basis to determine the condition of the X-ray tube. For example, if tungsten is deposited on the output window, the spectrum of the X-ray radiation provided by the X-ray tube may be changed, however, it may depend on the thickness of the deposit, and therefore depending on the length of the tungsten material. In order to evaluate whether the X-ray tube may be in a condition for further use or may be in a condition for maintenance, the filtration function is used to determine the status of the X-ray tube. Similar evaluations may be carried out for other filtrations of the X-ray radiation. For instance, in case liquid metal of the bearing causes the filtration, the condition of the X-ray tube may be evaluated as a condition for maintenance.

The X-ray system may comprise an X-ray system controller, which is configured to control the X-ray system, in particular the X-ray tube. Therefore, the X-ray system can be controlled in likewise manner for detecting the spectrally different reference-values and the spectrally different working-values. The spectrally different reference-values are determined at a predefined condition of the X-ray system, in particular when being newly assembled. Therefore, the corresponding reference data set representing the plurality of spectrally different reference-values may be stored in a storage means of the X-ray system. The spectrally different working-values are detected preferably at predefined operation intervals of the X-ray tube in order to evaluate the status of the X-ray tube in respective periods of time. Accordingly, the spectrally different working-values refer to the condition of the X-ray tube when being detected, thus at the respective operation interval. Consequently, the status of the X-ray tube can be observed during its use.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF THE EMBODIMENTS

Figure 1:
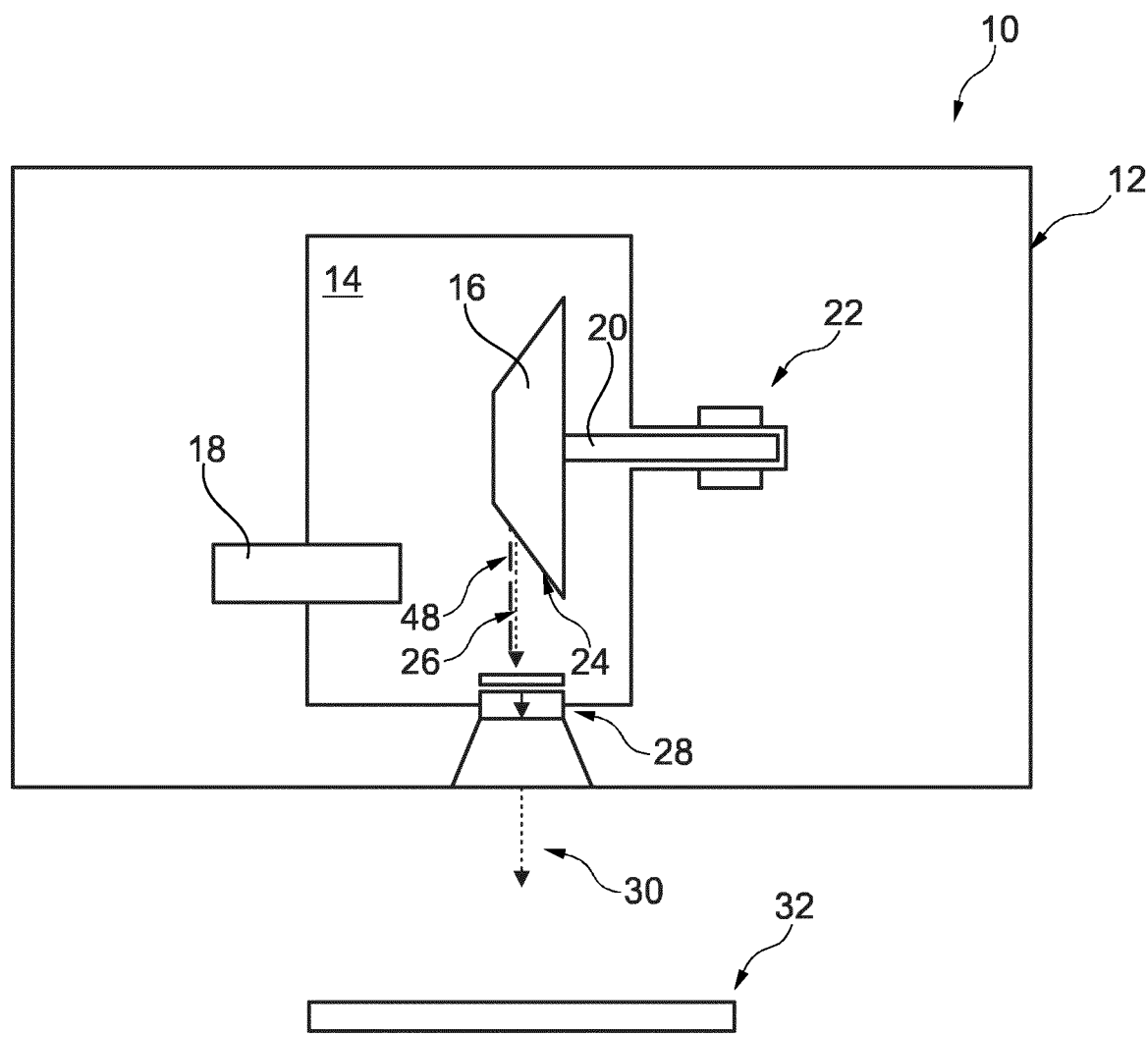
FIG. 1 schematically illustrates an X-ray tube and an X-ray detector arrangement.

FIG. 1 schematically illustrates an X-ray tube 10. The X-ray tube 10 comprises a housing 12, wherein the housing 12 forms a chamber 14. The X-ray tube 10 further comprises an anode 16 and a cathode 18. The anode 16 and the cathode 18 are arranged at least partly in the chamber 14. The anode 16 is coupled to a drive shaft 20. The drive shaft 20 belongs to a drive 22 of the X-ray tube 10. The drive 22 is configured to rotate the anode 16. The drive 22 comprises a bearing, such that the drive shaft 20 is rotatable. In operation, an electrical potential is applied across the cathode 18 and the anode 16. Further, the cathode 18 may be heated to an operation temperature. Furthermore, during operation, the anode 16 is rotated. Due to the electrical potential and the preferred heated cathode 18, the cathode 18 emits electrons, which traverse the gap between the cathode 18 and the anode 16. The emitted electrons impact the anode 16 at a focal spot 24, thereby generating source X-ray radiation 26. The source X-ray radiation 26 is at least partly directed to an output window 28 of the X-ray tube 10, wherein the output window 28 is configured to be passed by the source X-ray radiation 26. The source X-ray radiation 26 passing the output window 28 forms the X-ray radiation 30 provided by the X-ray tube 10.

FIG. 1 further schematically illustrates an X-ray detector arrangement 32. The X-ray detector arrangement 32 is arranged, such that at least a part of the X-ray radiation 30 impinges on the surface of the X-ray detector arrangement 32. A subject to be imaged can be arranged at an area between the output window 28 of the X-ray tube 10 and the X-ray detector arrangement 32.

The X-ray tube is shown schematically in FIG. 1 for illustrative purposes only. The invention may be utilized in connection with several of types of X-ray tubes or X-ray systems. Therefore, although the following discussion may refer to FIG. 1, it should be understood that the present invention is not limited to be carried out in connection with the X-ray tube 10 shown in FIG. 1.

Figure 2:
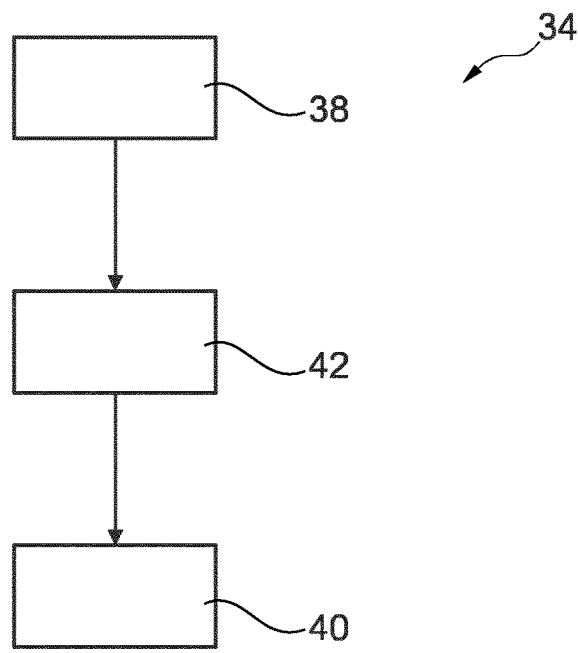
FIG. 2 schematically illustrates the device in one exemplary embodiment according to the present invention.
Figure 5:
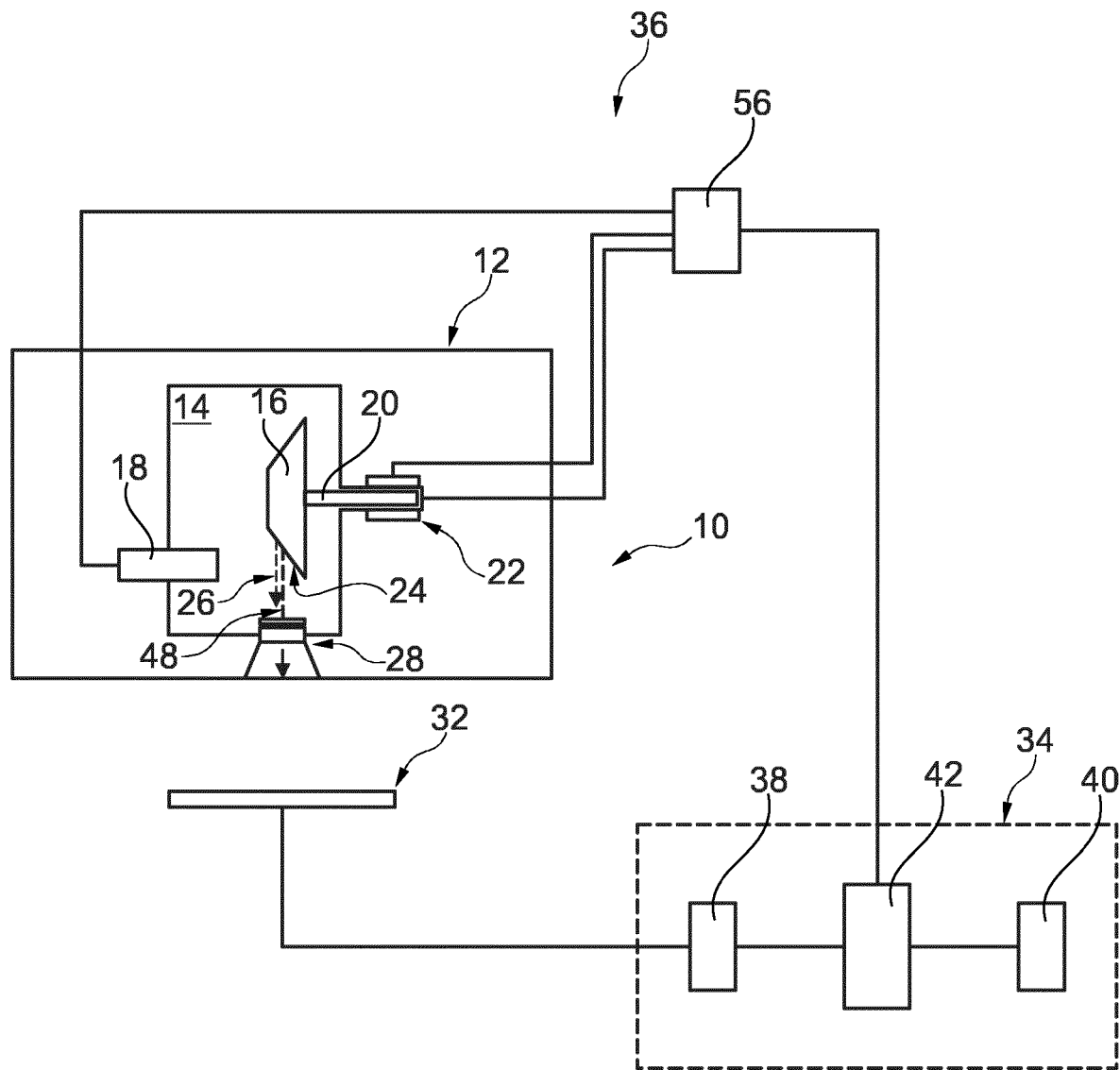
FIG. 5 schematically illustrates an example of an X-ray system according to the present invention.

FIG. 2 schematically illustrates an exemplary embodiment of the device 34 according to the present invention for determining a status of an X-ray tube 10 of an X-ray system 36 (schematically shown in FIG. 5). The device 34 comprises an input interface 38, an output interface 40 and a processing unit 42. The input interface 38 is configured to receive a reference data set representing a plurality of spectrally different reference-values 44 of a detected X-ray radiation 30 of an X-ray tube 10 under a predefined control scheme of an X-ray system 36. The input interface 38 is further configured to receive a working data set representing a plurality of spectrally different working-values 46 of a detected X-ray radiation of the X-ray tube 10 under the same predefined control scheme of the X-ray system 36, wherein an X-ray filtration, caused by a use of the X-ray tube 10, is applied at an X-ray radiation path 48 of the X-ray tube 10. The processing unit 42 is configured to determine, based on the reference data set and the working data set, a filtration function for the X-ray radiation 30 of the X-ray tube 10 indicating the X-ray filtration. The processing unit 42 is further configured to determine a status of the X-ray tube 10 based on the filtration function. The output interface 40 is configured to provide the status of the X-ray tube 10 for a further purpose.

In an example, the predefined control scheme refers to predefined settings of the X-ray system 36, in particular of the X-ray tube 10, and/or to a predefined operation plan for the X-ray system 36, in particular for the X-ray tube 10. The predefined settings for the X-ray tube 10 may relate to the electrical potential between the cathode 18 and the anode 16. Further, the predefined settings of the X-ray tube 10 may refer to the rotating velocity of the anode 16. Furthermore, the predefined settings of the X-ray tube 10 may refer to the waveform of the electrical potential between the cathode 18 and the anode 16, in particular to its frequency and/or amplitude. According to the operation plan for the X-ray tube 10, the electrical potential between the cathode 18 and the anode 16 may be adapted with respect to predefined time intervals, wherein for each time interval a predefined setting for the X-ray tube 10 may be applied. In an example, in a first time interval, a first electrical potential may be applied between the cathode 18 and the anode 16. In a second time interval, a second electrical potential, being different to the first electrical potential, between the cathode 18 and the anode 16 may be applied. The predefined settings and/or predefined operation plan may also comprise respective settings and/or sub-plans for the X-ray detector arrangement 32.

In order to provide reasonable data for determining the status of the X-ray tube, the control scheme may be used to acquire the spectrally different reference-values 44 and to acquire the spectrally different working-values 46. Accordingly, the reference data set and the working data set provide a good basis to determine the ageing of the X-ray tube 10, since the reference data set and the working data set are acquired under similar conditions referring to the same control scheme.

In an example, the spectrally different reference-values 44 are pre-acquired. Thus, the corresponding reference data set may relate to a reference condition of the X-ray tube 10.

The spectrally different working-values may be acquired at a predefined operation interval of the X-ray tube 10. Therefore, the spectrally different working-values 46 may refer to a condition of the X-ray tube 10 after a certain operation time of the X-ray tube 10.

In an example, the spectrally different reference-values 44 indicate or represent energies at different sub-spectrums of the X-ray radiation 30. For instance, one of these values may represent the energy of detected X-ray radiation 30 at a first electrical potential between the cathode 18 and the anode 16, for instance 80 kVp. Further, a further value of the spectrally different reference-values 44 may represent the energy of correspondingly detected X-ray radiation 30 at a second electrical potential between the cathode 18 and the anode 16, for instance 140 kVp. In likewise manner, the spectrally different working-values may indicate or represent energies at different sub-spectrums of the X-ray radiation. For instance, one value of the spectrally different working-values 46 may represent the energy of the detected X-ray radiation 30 at the first electrical potential between the cathode 18 and the anode 16. A further value of the spectrally different working-values 46 may represent the energy of the detected X-ray radiation 30 at the second electrical potential between the cathode 18 and the anode 16.

In an example, the device 34 is configured as a stand-alone device or as a part of a system, in particular the X-ray system 36.

In an example, the anode 16 may be, in particular mainly, made of tungsten. For instance, the anode 16 may comprise tungsten. Under electron bombardment, some tungsten may be able to escape from the anode 16. The electron bombardment may cause a surface at the focal spot 24 to become rough or its surface may become rougher. This effect may also be called as a heel effect. The electron bombardment may also cause some of the tungsten atoms to escape and being deposited on the output window 28 of the X-ray tube 10. Thus, source X-ray radiation 26 emitted by the anode 16 may be forced to traverse peaks at the rough surface at the focal plane 24 of the anode 16 and/or to traverse tungsten deposited on the output window 28 of the X-ray tube 10. Both effects may be equivalent to a filtration, in particular a tungsten filtration, of the source X-ray radiation 26 and thus may change the spectrum of the X-ray radiation 30 provided by the X-ray tube 10.

In an example, the bearing of the drive 22 of the X-ray tube 10 may be formed by a spiral-groove bearing. Further, the bearing of the drive 22 may comprise a liquid metal, in particular gallium-indium-tin. A leakage in the bearing of the drive 22 may cause a deposit of the liquid metal at the output window 28 of the X-ray tube 10. The deposit of the liquid metal at the output window 28 may be equivalent to a filtration of the source X-ray radiation 26 and thus may change the spectrum of the X-ray radiation 30 provided by the X-ray tube.

In a further example, the cathode 18 of the X-ray tube 10 may comprise a filament. A wear-out of the filament of the cathode 18 may cause a deposit of filament material at the output window 28 of the X-ray tube 10. In an example, the filament may be made of tungsten or comprise tungsten. Accordingly, a wear-out of the filament of the cathode 18 may cause a filtration, in particular a tungsten filtration, of the source X-ray radiation 26. The filament of the cathode 18 may be made or comprise other material than tungsten. In particular, the filament of the cathode 18 may comprise iron (Fe).

Accordingly, filament deposited at the output window 28 of the X-ray tube 10 may cause a different filtration. Consequently, a deposit of filament of the cathode 18 may be equivalent to a filtration of the source X-ray radiation 26.

In an example, the X-ray tube 10, in particular the chamber 14 and/or elements arranged therein, may comprise dopants and/or coatings. The dopants and/or coatings may also wear during use of the X-ray tube 10. Accordingly, dopants and/or coatings may be deposited on the output window 28 of the X-ray tube 10. In likewise manner as explained before, the dopants and/or coatings may cause a filtration of the source X-ray radiation 26 and thus may change the spectrum of the X-ray radiation 30 provided by the X-ray tube 10. In particular, the dopants and/or coatings may comprise barium and/or lead. Consequently, a deposit of dopants and/or coatings may be equivalent to a filtration of the source X-ray radiation 26.

In an example, the X-ray tube 10 may comprise a liquid cooling circuit, wherein a corresponding cooling liquid may comprise oil and/or lead. In case of a failure of the liquid cooling circuit, the liquid, in particular the oil, may enter the chamber 14 of the X-ray tube 10 and may be deposited at the output window 28 of the X-ray tube 10. In likewise manner as explained before, the cooling liquid, in particular the corresponding oil and/or lead, deposited at the output window 28 may be equivalent to a filtration of the source X-ray radiation 26 and thus may cause a change in the spectrum of the X-ray radiation 30 provided by the X-ray tube 10.

As explained above, the source X-ray radiation 26 may be subject to filtration due to different wear of the X-ray tube 10 and/or due a failure of the X-ray tube 10. Thus, a reference spectrum indicated by the reference data set may differ from a working spectrum indicated by the working data set. Accordingly, the reference data set and the working data set provide a basis to determine a filtration function representing the filtration caused by the wear or the failure of the X-ray tube. The filtration function may represent a transformation of the reference data to the working data, or vice versa, caused by the filtration. As an effect, the filtration function may indicate a filtration of an element or material, which may be arranged in the X-ray radiation path causing the respective filtration.

As a further effect, the filtration function may comprise the information about the type of the filtration, in particular with respect to the material causal for the filtration. Further, the filtration function may comprise the information about the extent of the filtration, in particular a decrease of a value correspondingly found in the reference-values 44 and the working-values 46. Further, the extent of the filtration may give information about the density and/or the length of the material causing the filtration.

As a further effect, the status of the X-ray tube can be determined based on the filtration function, since the filtration function may comprise the information about the type and/or the extent of the filtration. For instance, the filtration function may comprise the information about the material and/or thickness of a material which causes the filtration. Depending on the material and/or the thickness of the material, a condition and thus a status of the X-ray tube can be determined and/or evaluated. In particular, a very thin deposit of tungsten at the output window 28 of the X-ray tube 10 may have a small impact on the condition of the X-ray tube 10, wherein an increased thickness of the same material, in particular when being larger than a corresponding threshold thickness, may result in a different condition of the X-ray tube 10 and thus in a different status of the X-ray tube 10. The status of the X-ray tube 10 may be a value. However, the status of the X-ray tube may also comprise information about the material causing the filtration, its thickness and/or its density. In case the status of the X-ray tube 10 relates to a value, this value may relate to a predefined interval allowing to evaluate the value with respect to the condition of the X-ray tube 10.

Assuming the source X-ray radiation 26 provided by the anode 16 is filtered by a filtration material arranged in the X-ray radiation path 48 and causing a change of the source X-ray radiation 26 which results in the X-ray radiation 30 provided by the X-ray tube. Assuming further a knowledge of an actual filtration function representing the filtration material, and the knowledge about the source X-ray radiation signal 26 would be sufficient to calculate the X-ray radiation 30, which could be provided by the X-ray tube 10. Accordingly, assuming having knowledge of the X-ray source radiation 26 and the X-ray radiation 30 provided by the X-ray tube 10 may serve in turn as a basis to calculate the actual filtration function. However, the source X-ray radiation 26 is usually not known. But having knowledge of the reference data set may be assumed as an approximation of the X-ray source radiation 26. Further, the working data set may serve as an approximation of the X-ray radiation 30 provided by the X-ray tube 10. As an effect, having knowledge of the reference data set and the working data set may be assumed as a good basis for estimating the filtration function, which may be very similar to the actual filtration function for a filtration material arranged in the X-ray radiation path 48. In other words, since the source X-ray radiation 26 is unknown, the reference data set may be a good approximation for the source X-ray radiation 26 and the working data set may be a good approximation for the X-ray radiation 30 provided by the X-ray tube 10 and therefore may serve as the basis to calculate or determine the filtration function.

Figure 3:
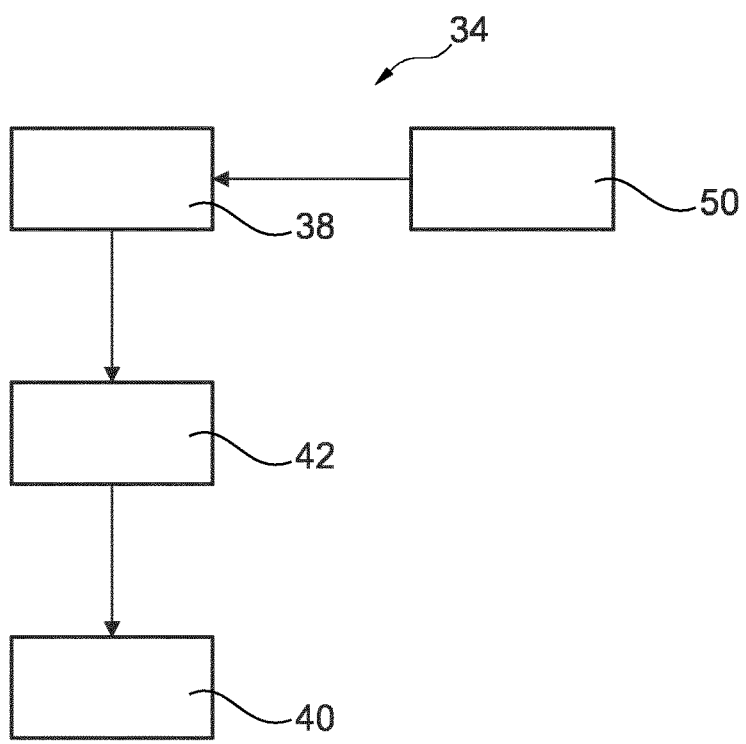
FIG. 3 schematically illustrates a further embodiment of the device according to the present invention.

FIG. 3 schematically illustrates a further exemplary embodiment of the device 34 according to the present invention.

In an example, the device 34 further comprises a storage means 50. The storage means 50 is configured to store the reference data set. Furthermore, the storage means 50 is configured to provide the reference data set to the input interface 38. Thus, the processing unit 42 may be configured to read the reference data set via the input interface 38 from the storage means 50.

In a further example, the input interface 38 may be part of the processing unit 42. Thus, the processing unit 42 may be configured to directly read the reference data set from the storage means 50.

As an effect, the reference data set may be pre-acquired and stored in the storage means 50, such that the detection of the spectrally different reference-values 44 is not necessarily to be carried out with the X-ray tube 10 when being outside of the production area of the X-ray tube 10. Instead, the acquisition of the reference data set may be integrated in the production process of the X-ray tube 10. Accordingly, just the spectrally different working-values 46 may be detected during predefined operation intervals of the X-ray tube 10, which may increase the usability of the device 34.

According to a further exemplary embodiment of the device 34, the processing unit 42 is configured to determine, based on the filtration function, an absorption spectrum, wherein the processing unit is configured to determine the status of the X-ray tube based on the absorption spectrum.

The absorption spectrum may indicate the absorption of an, in particular equivalent, absorption material, which cause the filtration of the source X-ray radiation 26. In other words, the filtration may cause the absorption spectrum, which may serve as the basis, or as a part thereof, to determine the status of the X-ray tube 10.

In an example, energy resolving measurements may be modeled with a set of equations, wherein each equation $$d_i \cong I_i \int_0^\infty R_i(E) D_i(E) F_i(E) e^{-Ls(E)} dE$$

is an estimation of one detector response, wherein di relates to the expected detector signal of measurement i, Ii relates to the x-ray tube current of measurement i, Ri(E) relates to the emission spectrum for measurement i (without the unknown filter effect), Di(E) relates to the spectral detector response for measurement i, Fi(E) relates to optional filtration spectra for measurement i, L relates to the length of the unknown filter material, and s(E) relates to the absorption spectrum of the unknown.

In an example, with this model and a set of detector measurements $d_i \leftarrow \tilde{d}_i$, the absorption spectrum and/or the absorption length may be determined.

In an example, the absorption length does not necessarily relate to the physical length of an absorption material. In particular, the absorption relates to a virtual or equivalent filtration, and thus the absorption length may relate to the length of a material or a thickness of a material relating to a virtual element arranged in the X-ray radiation path 48 causing an equivalent filtration.

Figure 4:
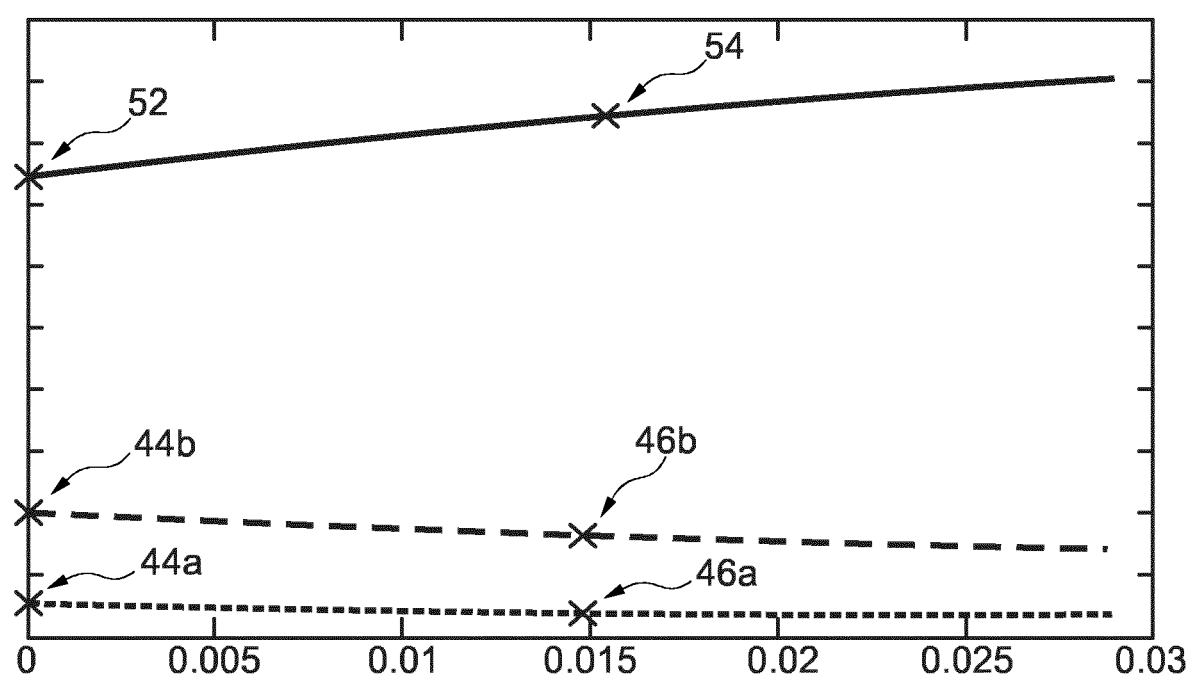
FIG. 4 schematically illustrates a spectrum diagram.

FIG. 4 schematically illustrates an ageing of an X-ray tube 10 based on the change of the X-ray radiation. The abscissa exemplarily indicates the length or the depth of an absorption material arranged on the output window 28 of the X-ray tube 10. After the production of the X-ray tube, no or almost no absorption material may be arranged on the output window 28. Thus, the length or thickness may be zero. Accordingly, the spectrally different reference-values 44 may be arranged in the diagram shown in FIG. 4 where the abscissa shows the value zero. A first reference-value 44a and a second reference-value 44b may be detected accordingly.

After using the X-ray tube 10, wear or ageing may occur at the X-ray tube 10. Correspondingly, and to be interpreted as an example, tungsten may be deposited on the output window 28 of the X-ray tube 10. Accordingly, the depth or length of the corresponding filtration material may increase. Thus, a further detection step may be carried out in order to acquire the working-values 46. The first working-value 46a and the second working-value 46b are exemplarily shown in FIG. 4 corresponding to the depth or length of the filtration material having a value of 0.015. The values of each data set refer to different electrical potentials between the cathode 18 and the anode 16.

In an example, the previously explained values corresponding to the reference data set and the working data set may be used to model two sets of equations, wherein each equation relates to the above explained equation. Having established these two equations, the length of the unknown filtration material may be calculated. Further, the absorption spectrum, which may also be determined based on the set of equations, may also serve as a basis to determine the absorption material.

According to an exemplary embodiment of the device according to the present invention, the processing unit 34 is configured to determine, based on the filtration function, an absorption length, wherein the processing unit 34 is configured to determine the status of the X-ray tube 10 based on the absorption length L.

In an example, the filtration may also correspond to an absorption length of the filtration material, which may also serve as a basis, or as a part thereof, to determine the status of the X-ray tube 10.

According to a further exemplary embodiment of the device 34 of the present invention, the processing unit 42 is configured to determine, based on the filtration function, an absorption material, wherein the processing unit 42 is configured to determine the status of the X-ray tube 10 based on the absorption material.

In an example, the filtration also corresponds to an absorption material for the filtration, which may also serve as the basis, or as a part thereof, to determine the status of the X-ray tube 10.

As an effect, specific materials may be evaluated differently and may cause a different status of the X-ray tube 10. For instance, if the absorption is caused by oil or lead, a determination of the status may be differently than determining tungsten as absorption material.

According to an exemplary embodiment of the device 34 according to the present invention, the processing unit 42 is configured to determine a further data set corresponding to a ratio of the reference data set and the working data set, or vice versa, wherein the processing unit 42 is configured to determine the filtration function based on the further data set.

As an effect, the ratio and thus the further data set may be flux-independent and provides thereof a good basis to estimate the filtration function. The corresponding ratio values 52, 54 are schematically illustrated in FIG. 4.

FIG. 5 schematically illustrates an exemplary embodiment of the X-ray system 36 according to the present invention. The X-ray system 36 comprises the X-ray tube 10, the X-ray detector arrangement 32, an X-ray system controller 56 and a device 34 as explained above. The X-ray system controller 56 is configured to control the X-ray system 36 according to the control scheme.

It is understood that, without repeating here all the examples and explanations provided with reference to the device 34 are also to be intended as being implemented by the X-ray system 36. Accordingly, advantages and/or effects achieved with the device 34 also can be achieved in an analogous manner by the X-ray system 36. Thus, reference is made to the explanations of the device 34 where it is suitable.

In an example, the X-ray system controller 56 may be configured to adjust the electrical potential between the cathode 18 and the anode 16. Further, the X-ray system controller 56 may be configured to adjust the waveform and/or the frequency of the electrical potential between the cathode 18 and the anode 16.

In a further example, the X-ray system controller 56 is configured to control the drive 22. In particular, the X-ray system controller 56 may be configured to control the rotation velocity of the drive shaft 20 and thus of the anode 16.

In an example, the X-ray system controller 56 may be configured to provide further adjustable settings for the operation of the X-ray system 36.

In an example, the X-ray system controller 56 may be configured to control the X-ray system 36 in accordance with an operation plan. The operation plan may provide the basis to adjust settings of the X-ray system 36 in accordance with predefined time intervals. For example, in a first time interval, the X-ray system controller 56 may control the X-ray system 36 such that a first electrical potential, for example 80 kVp, may be applied between the cathode 18 and the anode 16. In a second time interval, the X-ray system controller 56 may be configured to apply a second electrical potential, for instance 140 kVp, between the cathode 18 and the anode 16.

In an example, the X-ray system controller 56 is configured to control the X-ray system 36 in accordance to the control scheme, which has been used for acquiring the spectrally different reference-values 44 and thus the reference data set.

As an effect, the working data set can be acquired under equivalent conditions, under which the reference data set has been acquired.

According to an exemplary embodiment of the X-ray system 36 according to the present invention, the X-ray detector arrangement 32 is configured to detect the X-ray radiation 30 of the X-ray tube 10 under the control scheme resulting in the plurality of spectrally different working-values 46.

In an example, a first working-value 46a is detected with the X-ray detector arrangement 32, wherein a first electrical potential is applied between the cathode 18 and the anode 16. In a further example, the second working-value 46b is detected in a subsequent step, wherein a different electrical potential, preferably a higher electrical potential, is applied between the cathode 18 and the anode 16. Thus, both working-values refer to the same condition of the X-ray tube 10, in particular to a common condition of the filtration, which may be caused by the same filtration material. Using these working-values 46a, 46b in relation to the reference-values 44a, 44b, a respective filtration function can be determined, which may indicate the wear and/or the ageing of the X-ray tube 10.

According to a further exemplary embodiment of the X-ray system 36 according to the present invention, the X-ray system controller 56 is configured to control the X-ray system 36 in accordance with the control scheme, such that different X-ray tube voltages, which correspond to different X-ray tube voltages applied for detecting the reference-values, are subsequently applied for detecting the working-values 46. In an example, an X-ray tube voltage forms the electrical potential between the cathode 18 and the anode 16.

In an example, for acquiring the spectrally different reference-values 44, different X-ray tube voltages may have been applied between the cathode 18 and the anode 16, wherein for each of the different X-ray tube voltages at least one reference-value 44 is acquired. In order to acquire the working-values 46 under similar conditions of the X-ray system 36, the X-ray system 36 may be controlled by the X-ray system controller 56 under the same control scheme. The resulting, spectrally different working-values 46 and the spectrally different reference-values 44 provide a good basis to determine the filtration function.

As a further effect, a plurality of spectrally different working-values 46 can be detected, wherein at each X-ray tube voltage, at least one corresponding working-value 46 can be detected.

Figure 6:
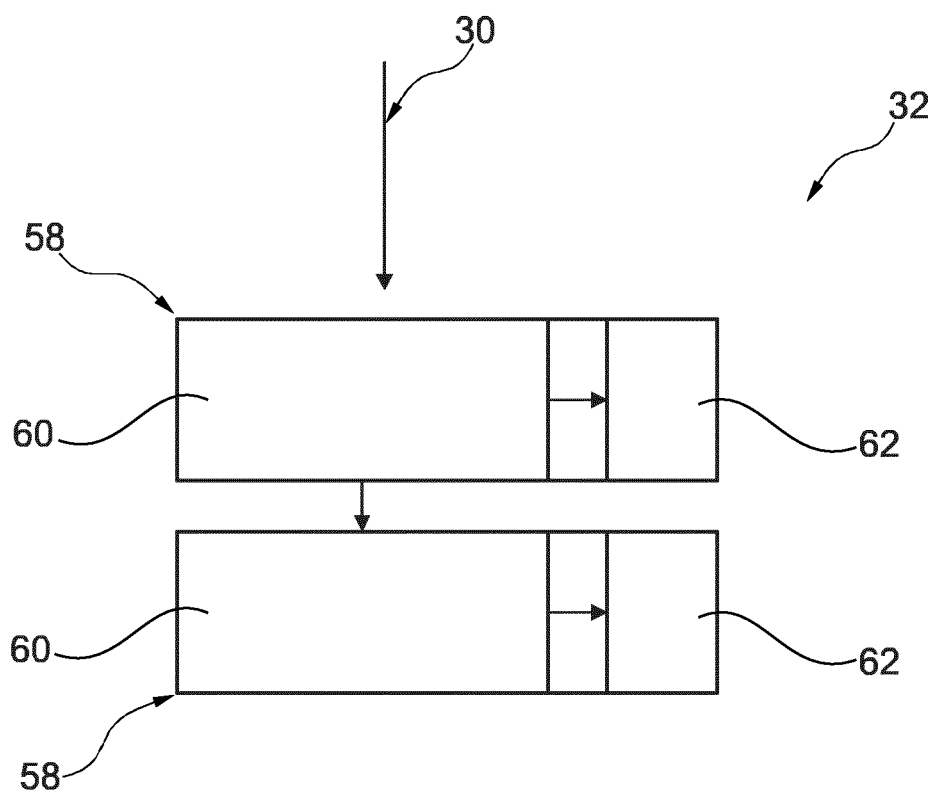
FIG. 6 schematically illustrates a first embodiment of the X-ray detector arrangement.

FIG. 6 schematically illustrates an exemplary embodiment of the X-ray detector arrangement 32.

In an exemplary embodiment of the X-ray system 36 according to the present invention, the X-ray detector arrangement 32 comprises a plurality of X-ray detector layers 58, wherein the X-ray system controller 56 is configured to control the X-ray system 36 in accordance with the control scheme, wherein the X-ray detector layers 58 comprise different effective responses, such that each X-ray detector layer 58 provides a detector sub-signal representing one of the working-values 46.

In an example, each X-ray detector layer 58 comprises a scintillator 60 and a photodiode 62. The scintillator 60 is preferably configured to emit light when being excited by the X-ray radiation 30 of the X-ray tube 10. The light of the scintillator 60 can be detected by the photodiode 62 of the corresponding X-ray detector layer 58.

In an example, the X-ray radiation 30 provided by the X-ray tube 10 may pass at least partly each of the X-ray detector layers 58.

In a further example, the effective response of an X-ray detector layer 58 corresponds to the absorption capability of X-ray radiation. For example, the X-ray detector layers 58 may have different energy absorption capabilities, and thus resulting in different effective responses when X-ray radiation 30 provided by the X-ray tube 10 passes the X-ray detector layers 58.

As an effect, a single X-ray detector arrangement 32 can provide the plurality of spectrally different working-values 46 during a single measurement time interval without changing the settings of the X-ray system 36.

Figure 7:
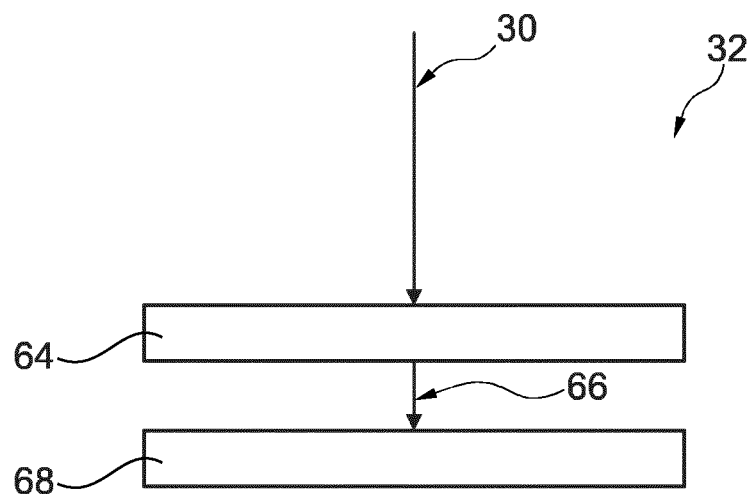
FIG. 7 schematically illustrates a second embodiment of the X-ray detector arrangement.

FIG. 7 schematically illustrates a further exemplary embodiment of the X-ray detector arrangement 32.

According to an exemplary embodiment of the X-ray system 36 according to the present invention, the X-ray detector arrangement 32 comprises a photon counting detector with energy discrimination configured to detect individual X-ray photons, to estimate its photon energy and to count these photons in respective energy bins, each representing an energy interval.

In an example, the X-ray detector arrangement 32 comprises a conversion element 64, which is configured to convert X-ray photons, impinging on the conversion element 64, and to emit electrically charged pulses 66.

In a further example, the X-ray detector arrangement 32 comprises an evaluation means 68, which is configured to estimate the photon energy based on the electrical charged pulses 66 provided by the conversion element 64. Further, the evaluation means 68 may be configured to count the estimated photon energies in respective energy bins fitting the estimated photon energy. Therefore, the estimated photon energies may be divided and assigned with the respective energy bin. Further, the counted, estimated photons assigned for each bin may provide the basis for the X-ray detector arrangement result. In other words, the number of counted photons for each energy bin may represent the corresponding working-values 46.

In a further example, the X-ray detector arrangement 32 is configured to detect the X-ray radiation 30 provided by the X-ray tube 10 at a plurality of detection steps and to assign each detected X-ray radiation 30 to one detector bin of a plurality of detector bins, if an energy of the detected X-ray radiation 30 is between a lower energy threshold and a corresponding upper energy threshold of the assigned bin. The bins may comprise a common lower energy threshold. For each of the plurality of detector bins, a corresponding lower energy threshold and a corresponding upper energy threshold may be predefined. Each detector bin may represent a spectrally energy section. The number of assigned detector X-ray radiations for a detector bin may represent a working-value for the respective spectrally energy section.

Figure 8:
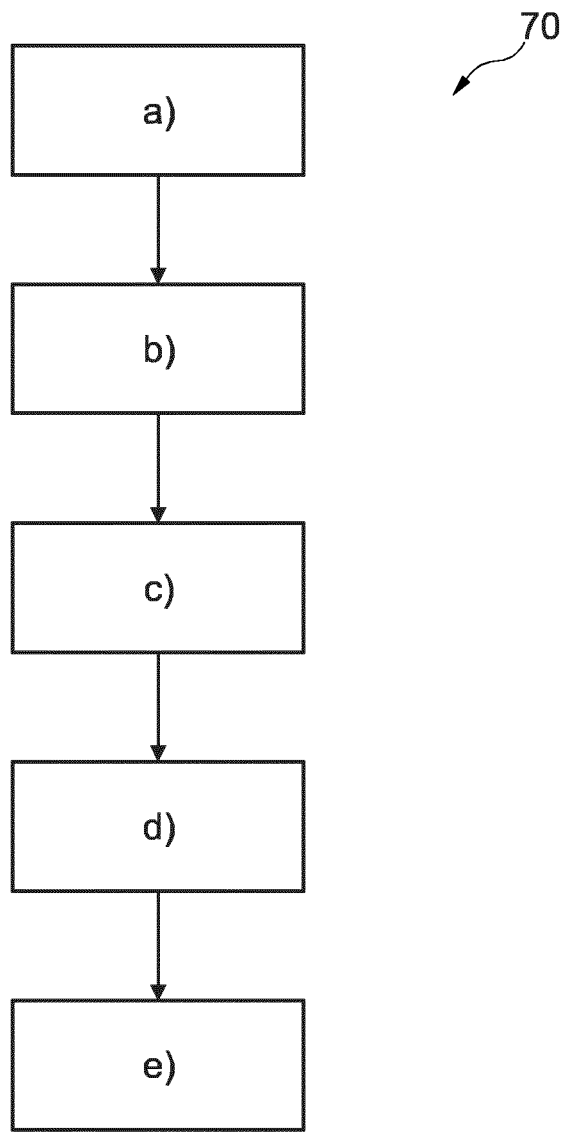
FIG. 8 schematically illustrates the state flow chart of the method according to the present invention.

FIG. 8 schematically illustrates an exemplary embodiment of the method 70 according to the present invention for determining a status of the X-ray tube 10 of the X-ray system 36, comprising the following steps:

In step a), a reference data set representing a plurality of spectrally different reference-values 44 of a detected X-ray radiation 30 of an X-ray tube 10 under a predefined control scheme of the X-ray system 36 is provided.

In a step b), a working data set representing a plurality of spectrally different working-values 46 of a detected X-ray radiation 30 of the X-ray tube 10 under the same predefined control scheme of the X-ray system 36 is provided, wherein an X-ray filtration, caused by a use of the X-ray tube, is applied at an X-ray radiation path 48 of the X-ray tube 10.

In a step c), based on the reference data set and the working data set, a filtration function for the X-ray radiation 30 of the X-ray tube 10 is determined indicating the X-ray filtration.

In step d), a status of the X-ray tube 10 is determined based on the filtration function.

In step e), the status of the X-ray tube is provided for a further purpose.

It is understood that, without repeating here all the examples, explanations and/or effects provided with reference to the device 34 and/or the X-ray system 36, the method 70 of the present invention is intended as being configured to carry out the method steps analogously provided before. Thus, all the above examples, explanations and effects, although firstly provided with reference to the device 34 and/or the X-ray system 36, are also to be intended as being implemented by the method 10.

In an example, method step c) comprises the sub-step of determining, based on the filtration function, an absorption length and/or an absorption material. Further, method step d) may comprise the sub-step of determining the status of the X-ray tube based on the absorption length and/or the absorption material.

According to a further exemplary embodiment of the present invention, a computer program element is provided, which, when being executed by a processing unit, is adapted to carry out the method described above.

According to a further exemplary embodiment of the present invention, a computer-readable medium having stored thereon a program element is provided.

The computer program element might be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

It has to be noted that embodiments of the invention are described with reference to different subject matters. In particular, some embodiments are described with reference to a device whereas other embodiments are described with reference to the method. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A detector or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for determining a status of an X-ray tube in an X-ray system, comprising:
    an input interface configured to receive a reference data set representing a plurality of spectrally different reference-values of a detected X-ray radiation of the X-ray tube under a predefined control scheme of the X-ray system; the input interface being configured to receive a working data set representing a plurality of spectrally different working-values of the detected X-ray radiation of the X-ray tube under the predefined control scheme of the X-ray system, wherein an X-ray filtration, caused by the X-ray tube, is applied at an X-ray radiation path of the X-ray tube;
    a processing unit configured to determine, based on the reference data set and the working data set, a filtration function for the X-ray radiation of the X-ray tube indicating the X-ray filtration; the processing unit being configured to determine a status of the X-ray tube based on the filtration function; the processing unit being configured to determine, based on the filtration function, an absorption spectrum; and
    an output interface configured to provide the status of the X-ray tube.

2. The device according to claim 1, wherein the processing unit is configured to determine, based on the filtration function, an absorption length; and wherein the processing unit is configured to determine the status of the X-ray tube based on the absorption length.

3. The device according to claim 1, wherein the processing unit is configured to determine a further data set corresponding to a ratio of the reference data set and the working data set; and wherein the processing unit is configured to determine the filtration function based on the further data set.

4. The device according to claim 1, wherein the processing unit is configured to determine, based on the filtration function, an absorption material; and wherein the processing unit is configured to determine the status of the X-ray tube based on the absorption material.

5. A method for determining a status of an X-ray tube of an X-ray system, comprising:
    providing a reference data set representing a plurality of spectrally different reference-values of a detected X-ray radiation of the X-ray tube under a predefined control scheme of the X-ray system;
    providing a working data set representing a plurality of spectrally different working-values of the detected X-ray radiation of the X-ray tube under the predefined control scheme of the X-ray system, wherein an X-ray filtration, caused by the X-ray tube, is applied at an X-ray radiation path of the X-ray tube;
    determining, based on the reference data set and the working data set, a filtration function for the X-ray radiation of the X-ray tube indicating the X-ray filtration;
    determining an absorption spectrum based on the filtration function; and
    determining the status of the X-ray tube based on the absorption spectrum and the filtration function.

6. An X-ray system, comprising:
    an X-ray tube;
    an X-ray detector;
    an X-ray system controller; and
    a device for determining a status of an X-ray tube in an X-ray system, comprising:
        an input interface configured to receive a reference data set representing a plurality of spectrally different reference-values of a detected X-ray radiation of the X-ray tube under a predefined control scheme of the X-ray system; the input interface being configured to receive a working data set representing a plurality of spectrally different working-values of the detected X-ray radiation of the X-ray tube under the predefined control scheme of the X-ray system, wherein an X-ray filtration, caused by the X-ray tube, is applied at an X-ray radiation path of the X-ray tube;
        a processing unit configured to determine, based on the reference data set and the working data set, a filtration function for the X-ray radiation of the X-ray tube indicating the X-ray filtration; the processing unit being configured to determine a status of the X-ray tube based on the filtration function; the processing unit being configured to determine, based on the filtration function, an absorption spectrum; and
        an output interface configured to provide the status of the X-ray tube;
    wherein the X-ray system controller is configured to control the X-ray system according to the predefined control scheme.

7. The X-ray system according to claim 6, wherein the X-ray detector is configured to detect the X-ray radiation of the X-ray tube under the control scheme resulting in the plurality of spectrally different working-values.

8. The X-ray system according to claim 7, wherein the X-ray system controller is configured to control the X-ray system in accordance with the control scheme, such that different X-ray tube voltages, which correspond to different X-ray tube voltages applied for detecting the reference-values, are subsequently applied for detecting the working-values.

9. The X-ray system according to claim 7, wherein the X-ray detector comprises a plurality of X-ray detector layers, wherein the X-ray system controller is configured to control the X-ray system in accordance with the control scheme; wherein the X-ray detector layers comprise different effective responses, such that each X-ray detector layer provides a detector sub-signal representing one of the working-values.

10. The X-ray system according to claim 7, wherein the X-ray detector comprises a photon counting detector with energy discrimination configured to detect individual X-ray photons, to estimate its photon energy, and to count these photons in respective energy bins, each of the bins representing an energy interval.

11. A non-transitory computer-readable medium having one or more executable instructions stored thereon, which when executed by a processor, cause the processor to perform a method for determining a status of an X-ray tube of an X-ray system, the method comprising:
    providing a reference data set representing a plurality of spectrally different reference-values of a detected X-ray radiation of the X-ray tube under a predefined control scheme of the X-ray system;
    providing a working data set representing a plurality of spectrally different working-values of the detected X-ray radiation of the X-ray tube under the predefined control scheme of the X-ray system, wherein an X-ray filtration, caused by the X-ray tube, is applied at an X-ray radiation path of the X-ray tube;

determining, based on the reference data set and the working data set, a filtration function for the X-ray radiation of the X-ray tube indicating the X-ray filtration;

determining an absorption spectrum based on the filtration function; and determining the status of the X-ray tube based on the absorption spectrum and the filtration function.

* * * * *